US006634752B2

(12) United States Patent
Curatu

(10) Patent No.: US 6,634,752 B2
(45) Date of Patent: Oct. 21, 2003

(54) DUAL-PATH OPTICAL SYSTEM FOR MEASUREMENT OF OCULAR ABERRATIONS AND CORNEAL TOPOMETRY AND ASSOCIATED METHODS

(75) Inventor: Eugene Curatu, Oviedo, FL (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/094,780

(22) Filed: Mar. 11, 2002

(65) Prior Publication Data

US 2003/0169403 A1 Sep. 11, 2003

(51) Int. Cl.[7] .................................................. A61B 3/10
(52) U.S. Cl. ........................................................ 351/212
(58) Field of Search ................................ 351/211, 212, 351/219, 246, 247, 160 R, 161, 177; 356/124; 606/4, 5

(56) References Cited

U.S. PATENT DOCUMENTS

| 5,062,702 | A | | 11/1991 | Bille |
| 6,271,915 | B1 | | 8/2001 | Frey et al. |
| 6,379,008 | B1 | * | 4/2002 | Chateau et al. ............. 351/247 |
| 6,460,997 | B1 | * | 10/2002 | Frey et al. .................. 351/211 |
| 6,467,906 | B1 | * | 10/2002 | Alpins ......................... 351/212 |

FOREIGN PATENT DOCUMENTS

WO 01/28410 4/2001

OTHER PUBLICATIONS

Malacara, "Optical Shop Testing," Second Edition, A Wiley– Interscience Publication, pps. 1–49, John Wiley & Sons, Inc., 1992.

* cited by examiner

Primary Examiner—George Manuel
(74) Attorney, Agent, or Firm—Allen, Dyer, Doppelt, Milbrath & Gilchrist, P.A.

(57) ABSTRACT

A unitary system for measuring both eye aberrations and corneal topography. includes a sensor for receiving wavefront data, a first optical path, and a second optical path. The first optical path includes means for introducing a collimated incident beam of radiation into the eye and for directing a wavefront exiting from the eye to the sensor as retinal wavefront data. Means are also provided for determining from the retinal wavefront data aberrations in the optical system. The second optical path includes means for introducing the incident beam onto the corneal surface and for directing a reflected beam therefrom to the sensor as corneal wavefront data. Means are additionally provided for determining from the corneal wavefront data a topography of an corneal surface. Finally, the system comprises means for switching the incident beam between the first and the second optical path.

42 Claims, 5 Drawing Sheets

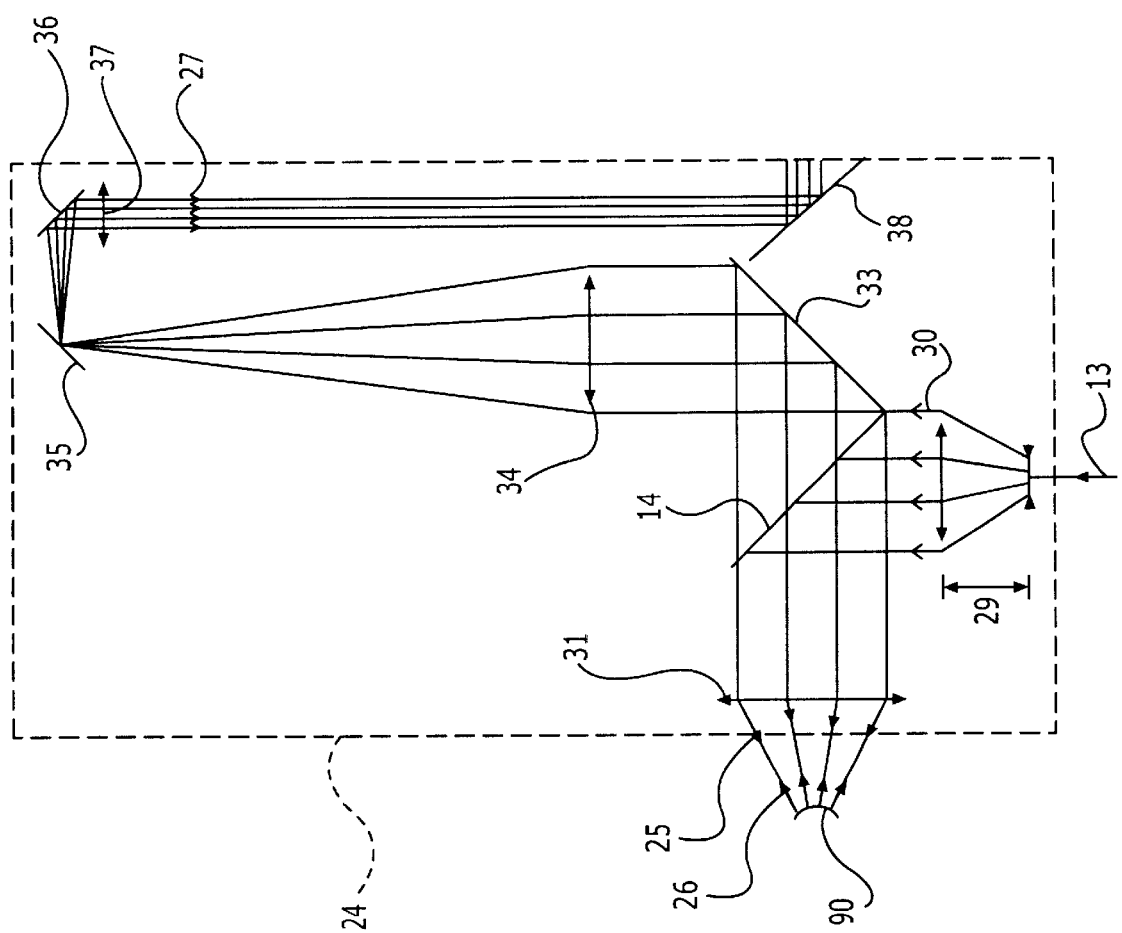

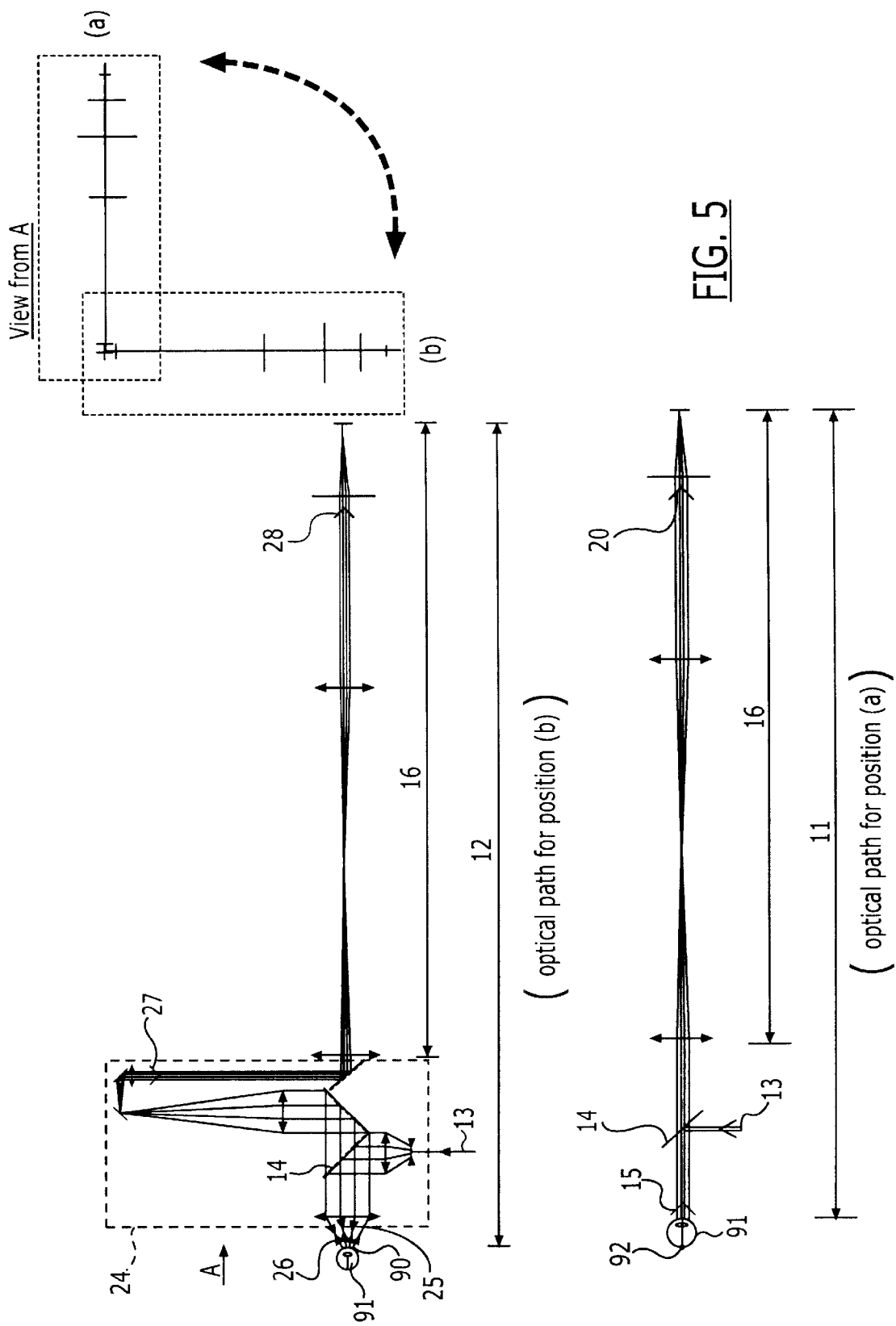

DUAL-PATH OPTICAL SYSTEM FOR MEASUREMENT OF OCULAR ABERRATIONS AND CORNEAL TOPOMETRY AND ASSOCIATED METHODS

BACKGROUND OF THE INVENTION

1. Field of the Invention

The present invention relates to optical measurement systems and methods, and, more particularly, to corneal topography and ocular aberrations measurement systems and methods.

2. Description of Related Art

Wavefront measurement systems are known in the art for measuring ocular aberrations, such as those taught by the assignee of the present invention (e.g., U.S. Pat. No. 6,271,915, the disclosure of which is incorporated hereinto by reference). An exemplary schematic for such wavefront measurements is given in FIGS. 2–6. in the '915 patent.

It is also known in the art to measure corneal topography (U.S. Pat. No. 5,062,702).

Finally, a system for measuring aberrations of spherical surfaces has been disclosed by M. V. Mantravadi ("Newton, Fizeau and Haidinger Interferometers," Chapter 1, Optical Shop Testing, $2^{nd}$ ed., D. Malacara, Ed., John Wiley & Sons, 1992). This system comprises a Fizeau-type interferometer.

SUMMARY OF THE INVENTION

It is therefore an object of the present invention to provide a system and method for measuring corneal topography.

It is a further object to provide such a system and method that also measures aberrations in the eye.

It is another object to provide such a system and method that share a common element along a portion of the optical path.

It is an additional object to provide a system and method for measuring aberrations in the eye and corneal topography with a unitary preparation.

It is also an object to provide a method for retrofitting an existing system for measuring aberrations of the eye to add a corneal topography measurement feature.

It is yet a further object to provide a method for making a system for measuring corneal topography.

It is yet another object to provide a method for making such a system that also measures aberrations in the eye.

These and other objects are achieved by the present invention, a unitary system and method for measuring both eye aberrations and corneal topography. The system comprises a sensor for receiving wavefront data, a first optical path, and a second optical path. The first optical path comprises means for introducing a collimated incident beam of radiation into the eye and means for directing a wavefront exiting from the eye to the sensor as retinal wavefront data. Means are also provided for determining from the retinal wavefront data aberrations in the optical system.

The second optical path comprises means for introducing the incident beam onto the corneal surface and means for directing a reflected beam therefrom to the sensor as corneal wavefront data. Means are additionally provided for determining from the corneal wavefront data a topography of an corneal surface.

Finally, the system comprises means for switching the incident beam between the first and the second optical path.

The method of the present invention comprises the step of selecting between a first and a second optical path. If the first optical path is selected, a collimated incident beam of radiation is focused adjacent a retina of an eye, and a reflected beam of radiation is transmitted to a sensor as an aberrated wavefront. Next the aberrated wavefront data are analyzed to characterize the aberrations.

If the second optical path is selected, the incident beam is directed to a corneal surface of the eye. The beam reflected from the corneal surface is transmitted to the sensor, and the corneal wavefront data are analyzed to characterize the corneal topography.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 4 is a closeup view of the topometer portion reducing the beam width reflected on the outer corneal surface at the same size as the beam exiting from the eye arising from the fovea center.

FIG. 5 is a schematic illustration of the tip-up mechanism.

DETAILED DESCRIPTION OF THE PREFERRED EMBODIMENTS

Figure 1:
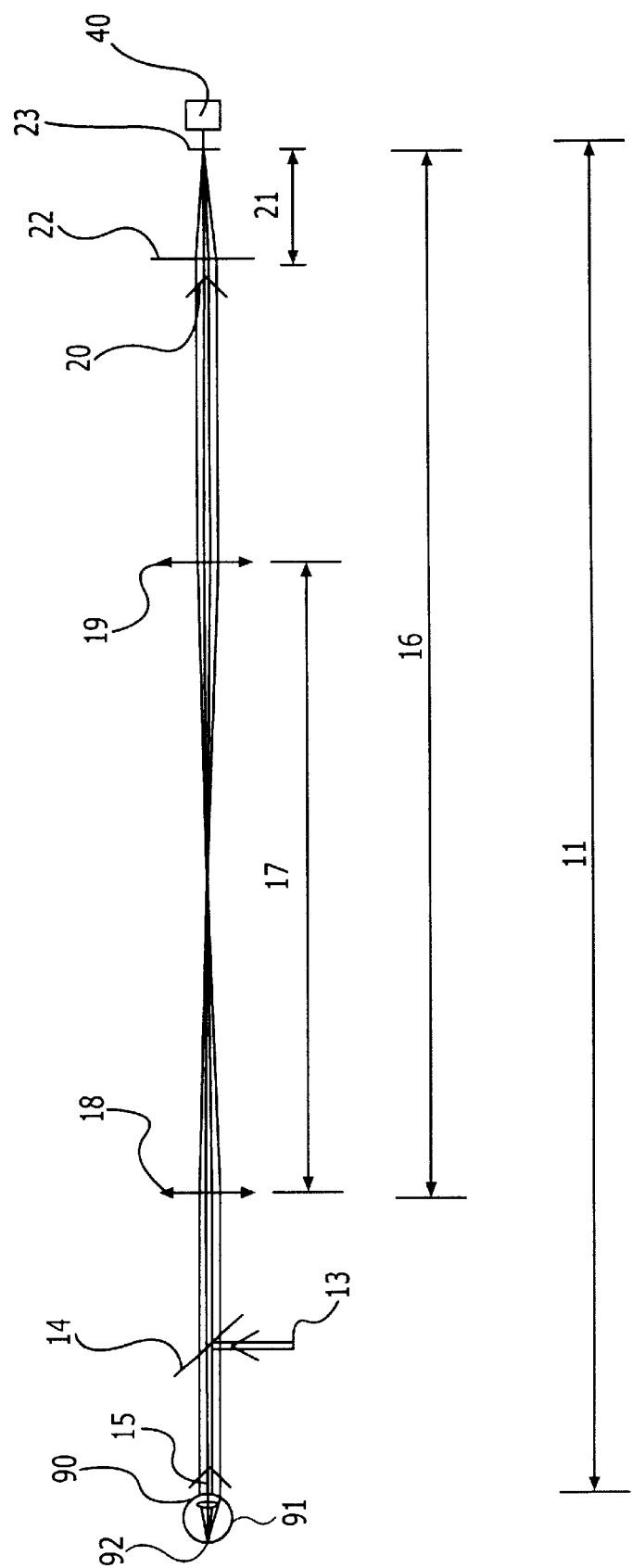
FIG. 1 is a schematic illustration of the aberrometer optical path of the present invention.
Figure 2:
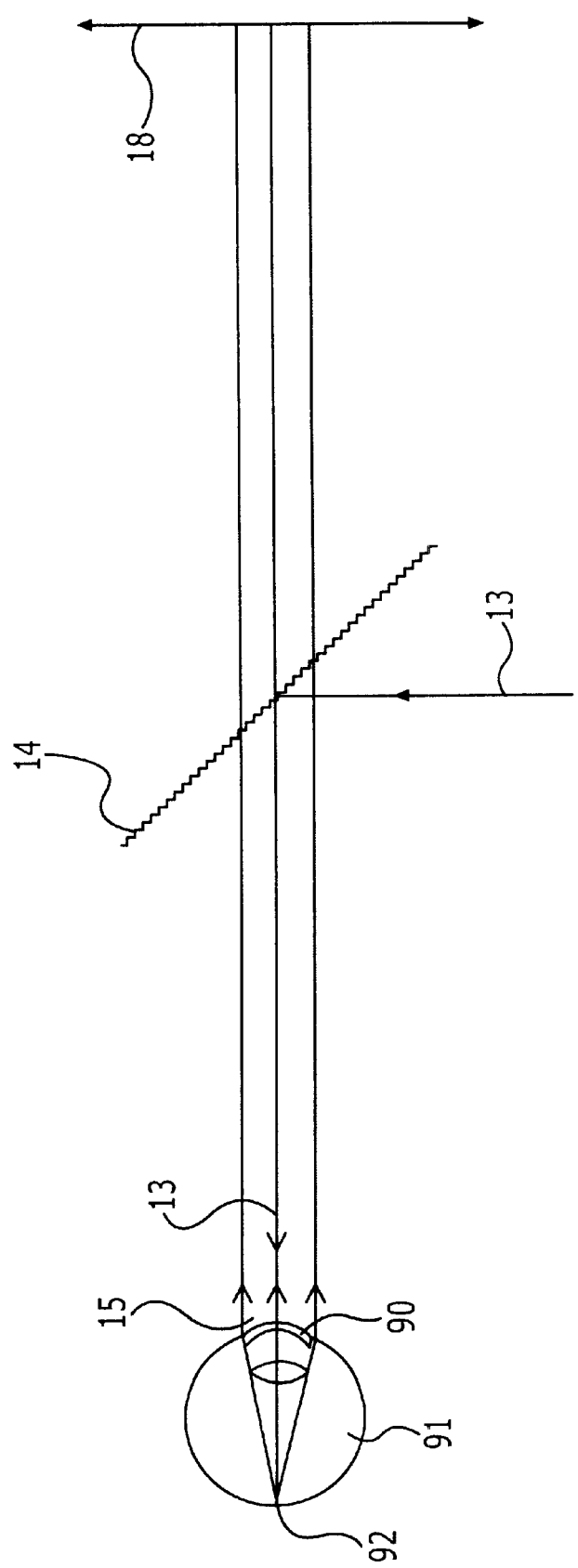
FIG. 2 is a close up view of the aberrometer portion launching the incident laser beam into the eye.
Figure 3:
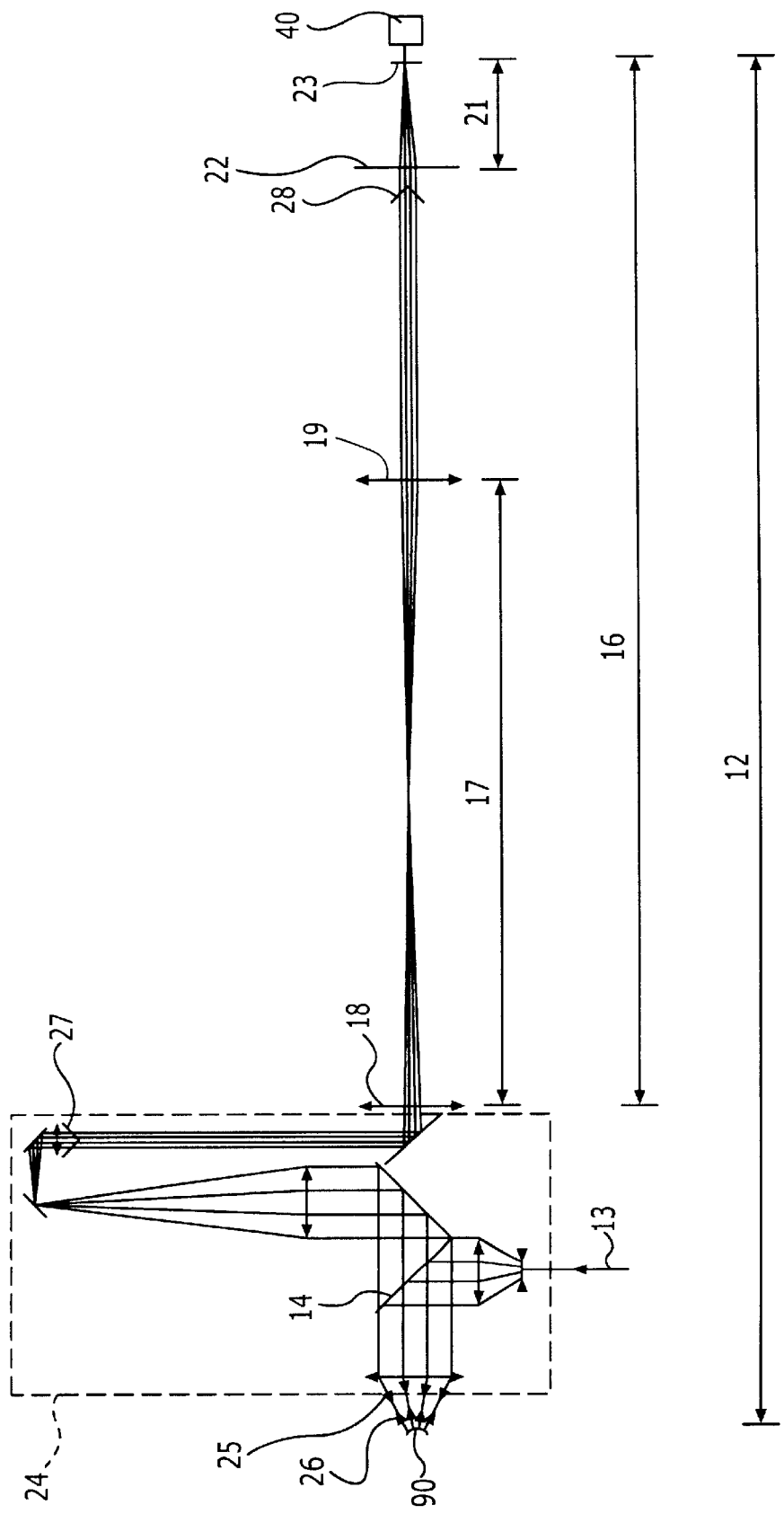
FIG. 3 is a schematic illustration of the topometer optical path.

A description of the preferred embodiments of the present invention will now be presented with reference to FIGS. 1–5.

A preferred embodiment of the system 10 of the present invention comprises a unitary system for measuring a topography of an optical surface and aberration in an optical system containing the optical surface. In a particular embodiment, the optical surface comprises an outer corneal surface 90, and the optical system comprises an eye 91.

The system of the present invention 10 comprises a first 11 and a second 12 optical path and means 24 for switching between these paths. The first optical path 11 (FIGS. 1 and 2) comprises a wavefront aberrometer such as is known in the art, such as that disclosed in commonly owned U.S. Pat. No. 6,271,915, although this is not intended as a limitation, and includes means for introducing a collimated incident beam 13 of radiation into the eye 91 and a common path 16. The incident beam 13 preferably comprises an eye-safe narrow laser beam. Specifically, the incident beam 13 introducing means of the first optical path comprises a beam splitter 14 that directs the incident beam 13 into the eye 91 to the fovea center of the retina 92. The wavefront reflected from the fovea center of the retina 92 by scattering travels back through intervening elements of the eye 91. The reflected beam 15 exiting from the eye 91, including the overall aberrations of the eye 91, travels the common path 16 toward the sensor 21 The sensor in a particular embodiment comprises a Hartmann-Shack wavefront sensor. In this embodiment the sensor 21 comprises a lenslet array, such as is known in the art, that samples the wavefront 20 or 28 at regularly spaced points.

The second optical path 12 (FIGS. 3 and 4) comprises a topometer that includes means for expanding a collimated incident beam of radiation 13, means for focusing the expanded beam 30, and means for directing a beam 32 reflected from the cornea 90 to the common path 16 of the system 10.

The expanding and focusing means comprises an afocal beam expander 29, a beam splitter 14, and a highly corrected focusing lens 31 that is adapted to transform the expanded beam 30 into a spherical wavefront 25 that converges at a center of curvature of the outer corneal surface 90. Specifically, the focusing lens 31 has a back focal length, e.g., 15 mm, greater than a radius of curvature of the corneal surface 90. The F/number of the first focusing lens 31 must be less than the nominal radius of curvature of the cornea surface divided by the pupil diameter, i.e., F/1.1. The distance between the focusing lens 31 and the corneal surface 90 determines the radius of curvature of the nominal sphere.

The wavefront 26 reflected back from the outer corneal surface 90 contains data on the departure of the corneal surface 90 from a nominal sphere.

The directing means of the second optical path 12 comprises an afocal relay subsystem formed by lenses 34 and 37 for reducing a diameter of the beam 32 to a size commensurate with the diameter of the reflected beam 15 of the first optical path 11. The directing means 24 also comprises a beam splitter 14 followed by a first mirror 33 that directs the beam 32 at a substantially right angle toward the first focusing lens 34 of the afocal relay system. The second mirror relay arrangement section comprises a second 35 and a third 36 mirror, which direct the beam reflected from the cornea 90 at a substantially 180° angle to the collimating lens 37. The third mirror relay arrangement section comprises a fourth mirror 38 that directs the collimated beam 27 at a substantially right angle to the common path 16 of the system 10.

The ratio of the effective focal lengths of the lenses 37 and 34 is approximately equal to the ratio between diameters of the beams 31 and 15. The beam 27 that is launched into the common path 16 has substantially the same diameter as the beam 15.

The switching means between a selected one of the first 11 and the second 12 optical paths comprises a tip-up mechanism that may be, for example, mechanical or electro-optical, which comprises a path-switching means 24 (FIG. 5). The path-switching means 24 of the present embodiment comprises a mechanical system comprising means for expanding a collimated incident beam of radiation 13, means for focusing the expanded beam 30, and means for directing the beam 32 reflected from the cornea 91 to the common path 16 of the system 10, as described previously related to the second, topometer path 12.

Once the first 11 and the second 12 optical paths are merged into the system 10, depending upon which has been selected, the beam 20 from the first, aberrometer optical path 11 or the beam 28 from the second, topometer optical path 12 travel a common path 16 toward the sensor 21 and the analytical system 40. The common path 16 comprises in the preferred embodiment an afocal relay subsystem 17 and the sensor 21. The afocal relay subsystem 17 is conceptually formed by, for example, but not intended to be limited to, a pair of lenses 18 and 19. In the aberrometer optical path 11 the afocal relay subsystem 17 images the corneal plane 90 onto the sampling aperture 22. In the second, topometer optical path 12 the afocal relay subsystem formed by lenses 34 and 37, together with the afocal relay subsystem 17, images the output plane of the lens 31 onto the sampling aperture 22.

In a preferred embodiment of the invention, using a Hartmann-Shack wavefront analyzer as is known in the art, at the back focal plane of the lens 19 of the relay system 17 is positioned an opaque plate having an aperture therein for transmitting a portion of the output wavefront therethrough. The aperture preferably comprises an aperture array 22 having a lens carried within each of a plurality of apertures in the aperture array forming a lenslet array, such as is known in the art. The sensor 21 further comprises a light-sensitive material 23 downstream of and in spaced relation to the lenslet array 22 for receiving samples of the wavefront 20 or 28 projected as a finite image thereon. Preferably the light-sensitive material 23 comprises a CCD array. Data received by the light-sensitive material 23 are then analyzed by computational software means 40 resident on a processor, such as known in the art.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A system for measuring aberrations and a topography of an eye comprising:
   a wavefront sensor;
   a first optical path comprising:
      means for introducing a collimated incident beam of radiation to a retina of an eye; and
      means for directing a wavefront reflected from a retina of the eye to the sensor;
   a second optical path comprising:
      means for introducing the incident beam to a corneal surface of the eye; and
      means for directing a wavefront reflected from the corneal surface to the sensor;
   means for switching the incident beam between the first and the second optical path; and
   means for transmitting wavefront data from the sensor to a processor for determining therefrom eye aberrations from first optical path wavefront data and a topography of the corneal surface from second optical path wavefront data.

2. The system recited in claim 1, wherein the introducing means of the first optical path comprises a beam splitter positioned along an optical axis to receive the incident beam from a radiation source and to direct the incident beam to the eye retina, the incident beam dimensioned to pass into a pupil of the eye, the beam splitter further adapted to pass a portion of the retina reflected wavefront along the optical axis, the sensor positioned along the optical axis.

3. The system recited in claim 1, wherein the sensor comprises a lenslet array.

4. The system recited in claim 3, wherein the sensor comprises a Hartmann-Shack wavefront sensor.

5. The system recited in claim 1, wherein the introducing means of the second optical path comprises means for expanding a diameter of the incident beam to a size commensurate with the corneal surface.

6. The system recited in claim 5, wherein the expanding means comprises an afocal beam expander.

7. The system recited in claim 1, wherein the introducing means of the second optical path comprises a beam splitter positioned along an optical axis to receive the incident beam from a radiation source and to direct the incident beam to the eye cornea, the beam splitter adapted to pass a portion of the cornea reflected wavefront along the optical axis, the sensor positioned along the optical axis.

8. The system recited in claim 1, wherein the introducing means of the second optical path comprises means for focusing the incident beam for transforming the incident beam into a spherical wavefront converging at a center of curvature of the corneal surface.

9. The system recited in claim 8, wherein the focusing means comprises a highly corrected focusing lens.

10. The system recited in claim 9, wherein the focusing lens has a back focal length greater than a radius of curvature of the corneal surface.

11. The system recited in claim 10, wherein the focusing lens has a back focal length greater than approximately 10 mm.

12. The system recited in claim 10, wherein the focusing lens has an F/number less than the radius of curvature of the cornea divided by a diameter of a pupil of the eye.

13. The system recited in claim 9, wherein the determining means comprises a software application for calculating from the wavefront data a departure of the cornea from sphericity.

14. The system recited in claim 1, further comprising software means resident on the processor for determining from the second optical path wavefront data a departure of the corneal surface from a nominal sphere.

15. The system recited in claim 1, wherein the second optical path directing means comprises an afocal relay system having means for reducing a diameter of the corneal reflected wavefront to a size substantially equal to a diameter of the retina reflected wavefront.

16. The system recited in claim 15, wherein the afocal relay system comprises first mirror means for removing the corneal reflected wavefront from an optical axis between the eye and the sensor and second mirror means for restoring the corneal reflected wavefront to the optical axis, and wherein the diameter reducing means comprises lens means.

17. The system recited in claim 16, werein the lens means comprises a focusing lens and a collimating lens downstream from the focusing lens.

18. The system recited in claim 1, wherein the wavefront sensor comprises a Hartmann-Shack wavefront sensor.

19. The system recited in claim 1, wherein the incident beam of radiation comprises an eye-safe optical laser beam.

20. The system recited in claim 1, further comprising a wavefront analyzer comprising:
an opaque plate having a sampling aperture therein for transmitting a portion of the output wavefront therethrough; and
a light-sensitive material downstream of and in spaced relation to the lenslet array sampling aperture for receiving the portion of the output wavefront projected as a finite image thereon.

21. The system recited in claim 20, wherein the sampling aperture comprises an aperture array and the light-sensitive material comprises a CCD array, and further comprising a lens carried within each of the plurality of apertures of the aperture array.

22. A method for measuring aberrations and a topography of an eye comprising the steps of:
introducing a collimated incident beam of radiation to a switching means;
manipulating the switching means for directing the incident beam to a first optical path or to a second optical path;
if the first optical path is selected:
introducing the incident beam to a retina of an eye; and
directing a wavefront reflected from a retina of the eye to a sensor;
if the second optical path is selected:
introducing the incident beam to a corneal surface of the eye; and
directing a wavefront reflected from the corneal surface to the sensor;
transforming sensor data into wavefront data; and
determining eye aberrations from first optical path wavefront data and a topography of the corneal surface from second optical path wavefront data.

23. The method recited in claim 22, wherein the introducing step of the first optical path comprises directing the incident beam to a beam splitter positioned along an optical axis, the beam splitter positioned to receive the incident beam from a radiation source and to direct the incident beam to the eye retina, the incident beam dimensioned to pass into a pupil of the eye, the beam splitter further adapted to pass a portion of the retina reflected wavefront along the optical axis, the sensor positioned along the optical axis.

24. The method recited in claim 22, wherein the sensor comprises an opaque plate having a sampling aperture therein.

25. The method recited in claim 22, wherein the sensor comprises a Hartmann-Shack wavefront sensor.

26. The method recited in claim 22, wherein the introducing step of the second optical path comprises expanding a diameter of the incident beam to a size commensurate with the corneal surface.

27. The method recited in claim 26, wherein the expanding step comprises directing the incident beam to an afocal beam expander.

28. The method recited in claim 22, wherein the introducing step of the second optical path comprises directing the incident beam to a beam splitter positioned along an optical axis to receive the incident beam from a radiation source and to direct the incident beam to the eye cornea, the beam splitter adapted to pass a portion of the cornea reflected wavefront along the optical axis, the sensor positioned along the optical axis.

29. The method recited in claim 22, wherein the introducing step of the second optical path comprises transforming the incident beam into a spherical wavefront converging at a center of curvature of the corneal surface.

30. The method recited in claim 29, wherein the transforming step comprises directing the incident beam to a highly corrected focusing lens.

31. The method recited in claim 30, wherein the focusing lens has a back focal length greater than a radius of curvature of the corneal surface.

32. The method recited in claim 31, wherein the focusing lens has a back focal length greater than approximately 10 mm.

33. The method recited in claim 31, wherein the focusing lens has an F/number less than the radius of curvature of the cornea divided by a diameter of a pupil of the eye.

34. The method recited in claim 22, further comprising the step of determining from the second optical path wavefront data a departure of the corneal surface from a nominal sphere.

35. The method recited in claim 22, wherein the second optical path directing step comprises reducing a diameter of the corneal reflected wavefront to a size substantially equal to a diameter of the retina reflected wavefront.

36. The method recited in claim 35, wherein the reducing step comprises removing the corneal reflected wavefront from an optical axis between the eye and the sensor prior to the reducing step and restoring the corneal reflected wavefront to the optical axis subsequent to the reducing step.

37. The method recited in claim 36, wherein the reducing step comprises using a focusing lens and a collimating lens downstream from the focusing lens.

38. The method recited in claim 22, wherein the sensor comprises a Hartmann-Shack wavefront sensor.

39. The method recited in claim 38, wherein the determining step comprises calculating from the wavefront data a departure of the cornea from sphericity.

40. The method recited in claim 22, wherein the incident beam of radiation comprises an eye-safe optical laser beam.

41. The method recited in claim 22, wherein the determining step comprises using a sensor comprising:

an opaque plate having an aperture therein for transmitting a portion of the output wavefront therethrough; and a light-sensitive material downstream of and in spaced relation to the opaque plate for receiving the portion of the output wavefront projected as a finite image thereon.

42. The method recited in claim 41, wherein the aperture comprises an aperture array and the light-sensitive material comprises a CCD array, and further comprising a lens carried within each of the plurality of apertures of the aperture array to form a lenslet array.

* * * * *